US010466156B2

(12) United States Patent
Chu et al.

(10) Patent No.: US 10,466,156 B2
(45) Date of Patent: Nov. 5, 2019

(54) OPTOFLUIDIC SORTER

(71) Applicant: BIO-RAD LABORATORIES, INC., Hercules, CA (US)

(72) Inventors: Daniel Y. Chu, Hercules, CA (US); Paul J. Patt, Danville, CA (US); Roger Tong, Berkeley, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 140 days.

(21) Appl. No.: 15/503,369

(22) PCT Filed: Aug. 19, 2015

(86) PCT No.: PCT/US2015/045924
§ 371 (c)(1),
(2) Date: Feb. 10, 2017

(87) PCT Pub. No.: WO2016/028907
PCT Pub. Date: Feb. 25, 2016

(65) Prior Publication Data
US 2017/0241888 A1   Aug. 24, 2017

Related U.S. Application Data

(60) Provisional application No. 62/039,584, filed on Aug. 20, 2014.

(51) Int. Cl.
*G01N 15/14* (2006.01)
*B01L 3/00* (2006.01)
*C12Q 1/04* (2006.01)
*G01N 15/10* (2006.01)

(52) U.S. Cl.
CPC .... *G01N 15/1404* (2013.01); *B01L 3/502761* (2013.01); *C12Q 1/04* (2013.01); *B01L 2200/0668* (2013.01); *B01L 2400/0424* (2013.01); *B01L 2400/0454* (2013.01); *G01N 2015/1006* (2013.01); *G01N 2015/1415* (2013.01)

(58) Field of Classification Search
None
See application file for complete search history.

(56) References Cited

U.S. PATENT DOCUMENTS

| | | | | |
|---|---|---|---|---|
| 5,521,384 A | * | 5/1996 | Lynch | G01N 21/05 250/343 |
| 5,995,209 A | * | 11/1999 | Ohman | G01N 21/05 356/246 |
| 6,228,652 B1 | * | 5/2001 | Rodriguez | G01N 15/14 356/335 |
| 7,951,580 B2 | | 5/2011 | Li et al. | |
| 2004/0080744 A1 | * | 4/2004 | Hobbs | B01L 3/502715 356/246 |
| 2008/0125838 A1 | | 5/2008 | Francis | |
| 2013/0224787 A1 | | 8/2013 | Durack et al. | |

FOREIGN PATENT DOCUMENTS

| | | |
|---|---|---|
| WO | 1999/044067 A1 | 9/1999 |
| WO | 2003/044483 A2 | 5/2003 |
| WO | 2005/100541 A2 | 10/2005 |

OTHER PUBLICATIONS

Extended European Search Report in Appln. 15834450.7 dated May 9, 2018; 12 pages.
Buican, et al., "Automated Single-Cell Manipulation and Sorting by Light Trapping", *Applied Optics*, vol. 26, No. 24; abstract, (Dec. 15, 1987).
Gallagher, et al., Charaterization of the Continuous, Differentiating Myeloid Cell Line (HL-60) From a Patient With Acute Promyelocytic Leukemia. *Blood*. vol. 54, No. 3, p. 715, paragraph 1, (Sep. 1979).
Voldman, et al., "Design and Analysis of Extruded Quadrupolar Dielectrophoretic Traps", *Journal of Electrostatics*, vol. 57; abstract, p. 69, paragraph 1; p. 70, paragraphs 1,4; p. 71, paragraph 3, p. 72, paragraphs 1,2,5; p. 76, paragraph 1; p. 79, paragraph 1; p. 83, paragraphs 3,4; figures 8,9, (2003).
International Patent Application No. PCT/US2015/045924, International Search Report and Written Opinion, dated Dec. 7, 2015, 10 pages.

* cited by examiner

*Primary Examiner* — Blaine Lankford
(74) *Attorney, Agent, or Firm* — Kilpatrick Townsend and Stockton LLP

(57) ABSTRACT

A method is provided for transporting a plurality of cells through a flow chamber, wherein the cells are initially immobilized on an internal surface of the flow chamber. The method comprises: selectively releasing the cells from the internal surface of the flow chamber; and flowing liquid through the flow chamber such that the released cells travel with the liquid, thereby transporting the cells through the flow chamber. Cells can be immobilized on or selectively released from the internal surface by applying or removing a trapping potential. The trapping potential can arise from an electric field gradient or an optical field gradient. Alternatively, cells can be selectively released from the surface using photocatalysis. Selective release allows cells to be individually observed or analyzed downstream, and can be based on a signal detected from one or more cells immobilized on the surface.

19 Claims, No Drawings

OPTOFLUIDIC SORTER

CROSS-REFERENCE TO RELATED PATENT APPLICATIONS

This application is the National Stage of International Application No. PCT/US2015/045924, filed Aug. 19, 2015, which claims the benefit of U.S. Provisional Application No. 62/039,584, filed Aug. 20, 2014, both of which are incorporated in its entirety herein for all purposes.

BACKGROUND OF THE INVENTION

Two cells derived from the same culture, line, species, organism, organ, or tissue can differ in terms of their genotypes, phenotypes, or patterns of gene expression. Variation in such attributes from one cell to the next can be of biological or medical interest. Accordingly, methods for handling and interrogating individual cells are now widely employed in biomedical research and pharmaceutical development. Microfluidic devices have been adapted for single-cell manipulations because they allow liquids, for example cell culture media, to be passed through channels and chambers having dimensions comparable to those of single cells. In microfluidic devices, cells can be tracked, sorted, characterized, subjected to treatments, or lysed to harvest material they contain. Other manipulations of single cells in these devices are possible.

Metering the passage of cells one by one through microfluidic devices, for example from a storage reservoir to an analysis site, is technically challenging, in part because of cellular adhesion. This phenomenon is the tendency of some cells to adhere to nearby surfaces or to each other. Cellular adhesion is governed by adhesion proteins in the plasma membranes or cell walls of individual cells, and is crucial to intercellular interactions and tissue function in vivo. In microfluidic devices, however, cellular adhesion can result in the undesired immobilization of cells on the internal surfaces of channels and chambers. To deter cellular adhesion, these surfaces can be passivated through chemical treatments or the application of microscopic textures. Surface passivation can be costly, and a given treatment may work under only a small range of experimental conditions. Alternatively, the immobilization of a cell on a microfluidic surface can be reversed by applying a force to the cell or changing its chemical environment. These actions, unless performed gently, can perturb the properties of the cell that are to be measured downstream, or alter the complement of biological molecules to be harvested from the cell.

BRIEF SUMMARY OF THE INVENTION

Provided herein is a method of transporting a plurality of cells through a flow chamber, wherein the cells are initially immobilized on an internal surface of the flow chamber. The method includes: selectively releasing the cells from the internal surface of the flow chamber; and flowing liquid through the flow chamber such that the released cells travel with the liquid, thereby transporting the cells through the flow chamber.

In some embodiments, the method further includes immobilizing the cells on the internal surface of the flow chamber prior to selectively releasing the cells. Immobilizing the cells can include applying a trapping potential. Selectively releasing the cells can include removing this trapping potential.

In some embodiments of the method, selectively releasing the cells includes applying a trapping potential.

In some embodiments, the internal surface of the flow chamber includes an electrode and the trapping potential arises from an electric field gradient. This trapping potential can result from dielectrophoresis. The electrode can be photoconductive and the trapping potential can be supplied by optoelectronic tweezers.

In some embodiments, the trapping potential arises from an optical field gradient. This trapping potential can be supplied by a focused laser beam, optical tweezers, or holographic optical tweezers.

In some embodiments of the method, the internal surface of the flow chamber includes a photocatalytic material and selectively releasing the cells includes illuminating the surface. In these embodiments, selectively releasing the cells can also include generating hydroxyl radicals or inducing a pH change in the vicinity of the surface. The internal surface of the flow chamber can also include a matrix layer containing a reagent that is pH-sensitive or reactive with hydroxyl radicals. The photocatalytic material can be titanium dioxide.

In some embodiments of the method, the cells are adherent. In some embodiments, the cells are non-adherent. In some embodiments, the cells are released one at a time. In some embodiments, at most 2, 5, or 10 cells of the plurality of cells are released simultaneously.

In some embodiments of the method, the flow chamber includes an outlet, the liquid is flowed toward the outlet, and the released cells arrive at the outlet one at a time. In some embodiments, the flow chamber includes an outlet, the liquid is flowed toward the outlet, and at most 2, 5, or 10 of the released cells arrive at the outlet simultaneously.

In some embodiments, the internal surface of the flow chamber is transparent.

In some embodiments, the method further includes detecting a signal from one or more cells immobilized on the internal surface of the flow chamber, wherein the cells are selectively released from the internal surface of the flow chamber based upon the signal. The signal can reflect the cell cycle phase, the viability, or the cell type of the one or more cells. The signal can reflect gene expression in the one or more cells.

DETAILED DESCRIPTION OF THE INVENTION

I. Overview

Light incident upon a flow chamber, such as a microfluidic channel, can be used in conjunction with liquid flow to meter the passage of single cells through the chamber. Through mechanisms discussed below, the light can mediate the mobility of individual cells in the chamber by immobilizing them on a surface of the chamber or dislodging them from the surface. Changes in the intensity of the light or other parameters can selectively release cells from the surface and into a liquid stream moving parallel to the surface. Cells can then be carried downstream, where they can be analyzed or observed one at a time or in desired groupings. Forces or chemical treatments to which the cells are subjected, as a result of the application of light, are gentle and minimally perturb the cells' physiology. The selective release of cells from the surface of a flow chamber can be based upon a signal detected from the cells while they are immobilized on the surface.

II. Definitions

"Metering" refers to means for controlling the entry of objects into a liquid stream or the passage of objects through a structure when suspended in a liquid stream. Metering can pertain to the timing or sequence with which objects enter the liquid stream, the separation between the objects, or the number of objects that pass a point in the structure over a certain period of time, for example.

"Immobilizing" refers to applying an external force to an object, thereby limiting the rate or extent of motion that the object can execute. The external force can be a trapping potential or a fluid drag force, for example. The external force can also be a restoring, adhesive, and/or tensile force exerted on the object if it is anchored to another object, such as a surface. The rate or extent of motion of an immobilized object is reduced relative to what the parameter would be in the absence of the external force.

"Selectively releasing" refers to reducing, removing, or counteracting the external force(s) immobilizing a particular object or group of objects while not significantly changing the external forces immobilizing other objects.

"Flow chamber" refers to a structure in which cells and liquid media can be retained, and through which the cells and media can flow. This term encompasses microfluidic channels and chambers, microscope flow cells, hemocytometers, and similar structures used in the observation and analysis of cells. "Internal surface" refers to a surface of the flow chamber that (i) is physically separated, by glass or another solid material, from the space outside the flow chamber, and (ii) can come into contact with cells and liquid media.

"Trapping potential" refers to a force field that confines or draws an object to a particular region of space. When confined to this region, the object is said to be "trapped".

"Dielectrophoresis" refers to the force exerted on a dielectric particle, and any movement resulting from such force, when the particle is placed in a non-uniform electric field.

"Optoelectronic tweezers", or equivalently "OET", refers to a system for manipulating dielectric particles using dielectrophoresis. The system includes a plurality of electrodes, at least one of which is photosensitive. A non-uniform electric field can be generated between electrodes of the plurality when an a.c. bias is imposed between them and light is incident on the photosensitive electrode.

"Optical trap" refers to the trapping potential associated with a focused laser beam.

III. Methods

The present methods provide for transporting a plurality of cells through a flow chamber, wherein the cells are initially immobilized on an internal surface of the flow chamber. The methods include the steps of selectively releasing the cells from the internal surface of the flow chamber, and flowing liquid through the flow chamber such that the released cells travel with the liquid.

The cells can be initially immobilized within the flow chamber by any available mechanisms. For example, the cells can stick or adhere to an internal surface of the flow chamber through electrostatic, Van der Waals, hydrophobic, or hydrophilic interactions between moieties on the cells and surface. Immobilization can be mediated by proteins, glycoproteins, sugars, or lipids on the cell surface, or any combination thereof. In some embodiments, immobilization occurs randomly as cells are retained in or pass through the flow chamber and interact with a surface of the chamber. If desired, particular surfaces within the flow chamber can be configured to induce immobilization of passing cells, such as with textures or chemical functionalities for which the cells have affinity. Surface micropatterning techniques useful for this purpose are reviewed in, for example, Kane et al., *Biomaterials* 20: 2363-2376 (1999) and El-Mi et al., *Nature* 442: 403-411 (2006). The mechanism of immobilization can be specific to certain cell types or cell-surface moieties, or on the other hand can be non-specific and general to many cell types.

The methods can include a step of immobilizing cells on the surface prior to selectively releasing the cells. This step can involve flowing a suspension of cells through the flow chamber and allowing random immobilization, such as surface sticking or adhesion, to occur. Alternatively, the step can involve actively inducing immobilization. For example, a chemical can be introduced in the flow chamber to cross-link moieties on the surfaces of the cell and flow chamber. As another example, an external stimulus can be applied to the cells, in the form of a pulse of light or a ligand for a cell-surface protein, to accelerate physiological processes related to cellular adhesion. Cells can be immobilized using any desired procedure. Cells can be submerged in a liquid medium during immobilization and remain submerged during selective release and transport through the flow chamber.

In some embodiments, cells are initially immobilized due to the application of a trapping potential. The potential can confine a cell to a region near or coincident with the surface of the flow chamber, such that a force is required to remove the cell from this region. The trapping potential is preferably large enough that the forces required to remove the cell from the desired region exceed any other forces the cell may experience while the potential is applied. Such other forces include, for example, drag forces resulting from fluid flow around the cell. The trapping potential can be applied for enough time to allow the cell to adhere or otherwise stick to the surface, or until such time as the selective release of the cell is desired. A trapping potential can arise from an electric field gradient or optical field gradient, for example, and can result from light incident upon the flow chamber.

In some embodiments, the trapping potential results from dielectrophoresis. The potential can be imposed by placing two or more electrodes within or adjacent to the flow chamber and introducing a non-uniform electric field between them. Preferably, one of the electrodes is located at a surface of the flow chamber, and dielectrophoresis draws cells toward this electrode. Upon exposure of the cell to the electric field, a dipole is induced in the cell, and a dielectrophoretic force acts on the cell due to coupling between this dipole and the electric field gradient. The magnitude and direction of the dielectrophoretic force depend on the size, permeability, and polarizability of the cell, the polarizability of the medium in which the cell is submerged, the frequency of the electric field, and other factors. Accordingly, the same electrode can either attract or repel a particular cell under different conditions. Any electrodes, including fixed metal electrodes or a two-dimensional electrode array, can be used to generate the electric field, although preferably one electrode is photoconductive, as described below.

Optoelectronic tweezers (OET) can be used in some embodiments to supply a dielectrophoretic trapping potential. The OET technology is described in detail in, for example, Chiou et al., *Nature* 436: 370-372 (2005); Ohta et al., *IEEE Journal of Selected Topics in Quantum Electronics* 13: 235-243 (2007); Wu, *Nature Photonics* 5: 322-324 (2011); and WO 2010/115167 A2. All of these documents are incorporated herein by reference. Briefly, a photoconductive electrode (including, in some cases, a phototransistor) and a transparent electrode are placed on opposite sides of the flow chamber and an a.c. bias is imposed between them. Light, for example incoherent light from a light-emitting diode, is then directed onto the photoconductive electrode, and a non-uniform electric field is generated between the illuminated region of this electrode and the transparent electrode. A digital micromirror device (DMD) microdisplay can be used to generate a patterned image of arbitrary shape, for example circles or squares, that can be projected onto the photoconductive electrode with the light source. Thus, the shape of the non-uniform electric field, and in turn the trapping potential, can reflect the shape of this image. By reprogramming the DMD microdisplay, the image can be dynamically reshaped to manipulate multiple cells in concert. For example, the cells can be corralled or moved across the surface of the flow chamber, or one cell can be released while others remain immobilized. In addition, different types of cells, and cells in different physiological states (e.g., live and dead) can be distinguished on the basis of their polarizabilities and Clausius-Mossotti factors.

In some embodiments, the trapping potential arises from an optical field gradient. Such a trapping potential can be supplied by one or more laser beams that are incident upon the flow chamber and each tightly focused with a high numerical aperture objective lens. The trapping potential is referred to as an optical trap. Each beam can trap a cell at the focus due in part to the cell scattering and refracting the laser light. The laser optics and flow chamber can be configured to position the focus of the laser beam near a surface of the flow chamber. Thus, when the laser is turned on, the trapping potential can grab a cell out of the aqueous medium in the flow chamber and immobilize it on the surface. Once in contact with the surface, the cell can stick or adhere to the surface, such that the cell's movement is restricted by both the trapping potential and interactions between the cell and the surface.

The physics and various implementations of optical traps are described, for example, in Neuman and Block, *Review of Scientific Instruments* 75: 2787-2809 (2004), and Grier, *Nature* 424: 21-27 (2003). A method of using optical traps to immobilize particles suspended in solution is disclosed in co-pending, co-assigned U.S. patent application Ser. No. 13/340,504, entitled "Hybrid Single Molecule Imaging Sorter". These documents are incorporated herein by reference.

In the present methods, two or more optical traps, collectively referred to as optical tweezers, can be used to manipulate a plurality of cells in the flow chamber independently or in concert. For example, one trap can be turned off to allow a cell to flow away, while another trap can be turned on to immobilize a cell. Alternatively, two traps can be used to push two cells toward each other or in a common direction. A single laser beam can give rise to two or more optical traps, for example by splitting the beam into two paths by orthogonal polarization. The paths can be independently steered and modulated using mirrors, lenses, optical modulators, optical deflectors, electromechanical devices, and/or shutters. Multiplexed arrays of optical traps called holographic optical tweezers can also be produced using diffractive optics or by time-sharing the light from one or more laser beams in multiple locations. Optical traps used herein can have any desired shapes or mode structures. The traps can also be controlled as desired. For example, the optical elements used to generate a trap can be controlled by computer, and the flow chamber can be monitored using a camera or microscope to track cells and provide input for controlling the traps.

Any of the trapping potentials discussed herein can be used to selectively release as well as immobilize cells on the internal surface of a flow chamber. In some cases, such as when the cells are non-adherent, a cell can be selectively released from the internal surface simply by removing the trapping potential. In the absence of a trapping potential, any interactions that remain between the cell and the internal surface can be weaker than forces acting on the cell due to Brownian motion or liquid flow. Thus, these interactions can be spontaneously broken, and the cell can be transported away from the site where it was trapped and through the flow chamber. When the trapping potential is supplied using optoelectronic tweezers, the potential can be removed by turning off the light incident upon the photoconductive electrode, thereby removing the non-uniform electric field within the flow chamber. Alternatively, the image projected on the photoconductive electrode can be reshaped so that the non-uniform electric field no longer traps the cell to be released. When the trapping potential is supplied using a laser beam in the form of one or more optical traps, the potential around a particular cell can be removed by blocking the laser or steering it away from the cell.

A cell immobilized on the surface of a flow chamber can also be selectively released by applying a trapping potential, such that the cell is drawn away from the surface. This mechanism of release can be useful when cells stick or adhere to the surface, such that removing any trapping potential used for immobilization is not sufficient to achieve release. If desired, the same kind of trapping potential used for immobilization can be used later for selective release. For example, in the case of OET, the frequency of the electric field can be changed, such that the direction of the force acting on the cell is reversed. Thus, a cell that is initially drawn to the photoconductive electrode (under "positive OET") can instead be repelled (under "negative OET"), and pushed away from the surface to which this electrode is closest. In the case of optical trapping, the relative positioning of a laser beam and flow chamber can be changed such that the focus of the beam moves away from the surface and toward the interior of the flow chamber. Thus, a cell affixed to the surface is pulled off and inserted into the stream of liquid passing through the flow chamber. Once the cell is liberated from the surface, the laser beam can be blocked.

Configuring a trapping potential for use in both immobilization and selective release can be convenient and straightforward, and provides a way to manipulate individual cells with a high degree of precision and control. However, it will be recognized that the selective release of a cell using a trapping potential need not be preceded by immobilization of that cell with the same trapping potential, or with a trapping potential at all. For example, a cell can be immobilized on the surface of the flow chamber through non-specific interactions or cellular adhesion, and then be selectively released using negative OET at a desired time. Generally, trapping potentials used in the present methods can be turned on or off, or reconfigured, in any desired sequence to immobilize and release cells.

A trapping potential can be used to immobilize or selectively release a cell by applying a force to that cell in any direction. For example, a trapping potential can apply a force to a cell in a direction parallel to the surface on which it is immobilized, as well as (or instead of) in a direction perpendicular to this surface. Electrodes for dielectrophoresis, including at least one photosensitive electrode, can be laid out next to each other or interdigitated on one internal surface of a flow chamber. Illuminating this surface while applying an a.c. bias between the electrodes produces an electric field parallel to the surface, which can exert lateral forces on cells immobilized near the electrodes. Systems used for this procedure are called lateral-field optoelectronic tweezers (LOET), and are discussed in more detail in Ohta et al., *IEEE Journal of Selected Topics in Quantum Electronics* 13: 235-243 (2007), and elsewhere. An optical trap can be used to exert lateral force on an immobilized cell by positioning the trap near the cell and just off the surface of the flow chamber.

In some embodiments of the present methods, cells are selectively released using photocatalysis, a phenomenon reviewed in Linsebigler et al., *Chemical Reviews* 9:5: 735-758 (1995) and elsewhere. The cells are first immobilized, using any desired mechanism or procedure, on an internal surface of the flow chamber containing a photocatalytic material. A non-limiting example of a photocatalytic material is titanium dioxide ($TiO_2$). To release cells of interest, a portion of the surface near these cells is illuminated with short-wavelength (i.e., blue or near-UV) light. Appropriate wavelengths include 388 nm or 418 nm, for example, although a skilled artisan will recognize that wavelengths above 400 nm cause less damage to cells. Preferably, when the internal surface occurs on a wall of the flow chamber, the incident light originates from the opposite side of the wall relative to the internal surface. Thus, the light does not pass through the cells before striking the photocatalytic material, and damage to the cells resulting from direct exposure to the light is reduced.

The short-wavelength light activates the photocatalytic material, which releases hydroxyl radicals and protons in the vicinity of the surface and the cells of interest. The released species can react with and disrupt chemical moieties anchoring the cells to the surface, causing the cells to detach. In some cases, activation of the photocatalytic material and cell detachment is accompanied by a pH change. The internal surface of the flow chamber can also include a matrix layer containing a reagent that is pH-sensitive or reactive with the hydroxyl radicals, and the anchoring moieties can be disrupted through secondary reactions. The light source is preferably collimated and, when incident on the internal surface of the flow chamber, subtends a small area of this surface. Thus, only a small number of cells is exposed to the light source at once, and selective release is achieved by targeting or sweeping the light source over cells of interest.

Photocatalysis can also be used to selectively kill cells in some embodiments. Cells can be killed upon exposure to the hydroxyl radicals released by the activated photocatalytic material, or by products of secondary reactions of these radicals. Cells can be simultaneously killed and released, or killed for the purpose of distinguishing between cells of interest and cells not of interest. It will be recognized that the conditions needed to selectively release and/or kill immobilized cells depend on characteristics of the photocatalytic material, any matrix layer, the cells themselves, and the mode of immobilization.

Any cell types can be used in the present methods. The cells can be prokaryotic, eukaryotic, plant, animal, mammalian, or human, for example. Cells can be adherent or non-adherent. It will be recognized that different cell types have different requirements for handling, culturing, and plating, and can be immobilized on surfaces and subsequently released under different conditions. For example, different cell types exhibit a broad range of electric polarizabilities, refract light to various degrees, and are differentially sensitive to fluid shear forces and hydroxyl radicals. Accordingly, the details of the present methods depend on the type of cells being transported through the flow chamber. In some embodiments, all cells from the plurality are derived from the same species, individual, organ, or tissue.

In the present methods, any liquids can be used that allow immobilization and selective release of cells in the flow chamber, and deliver the cells in a desired physiological state for downstream analysis. Examples of liquids that can be used include water, saline, buffer, cell growth or culture medium, blood plasma, or serum. In some embodiments, a liquid is selected to be roughly isotonic with cells in the flow chamber to prevent swelling or shrinkage. When a trapping potential is supplied as an electric field gradient to immobilize or selectively release cells, the liquid in the flow chamber can be chosen to have a desired conductivity relative to the cell cytoplasms. For example, the liquid can contain uncharged osmolytes (e.g., sucrose and dextrose) and have a lower conductivity than most cell types, so that cells can be manipulated using positive OET.

Cells can be submerged in the same liquid during immobilization, selective release, and transport through the flow chamber, or different liquids can be used at different steps. For example, the liquid present when the cells are immobilized on the surface of the flow chamber can be displaced with a new liquid before the cells are selectively released. This new liquid can in turn be displaced by the liquid that is flowed through the flow chamber to transport the released cells. Thus, flowing liquid through the flow chamber can involve displacing or 'chasing' a suspension of cells previously released. In other embodiments, however, selective release and flow occur simultaneously. Liquids can be introduced into, removed from, and flowed through the flow chamber as desired and as appropriate for the configuration of the flow chamber.

The selective release of cells from the surface of the flow chamber can harness any of the mechanisms discussed above, and can be metered as desired. For example, cells can be released one at a time or in groups. In some embodiments, at most 2, 5, or 10 cells of the plurality of cells are released simultaneously. The timing of release can be set in concert with the liquid flow rate to achieve a desired frequency of cells being transported through the flow chamber. In some embodiments, this frequency is kept low enough to allow cells to be individually observed or analyzed downstream, and cell-to-cell differences to be detected. Cells can be treated as desired after they have been transported through the flow chamber and exit the flow chamber. For example, cells can be lysed, treated with a drug, or optically interrogated.

The flow chamber can be part of a larger liquid-handling system, such as a microfluidic device or a flow cytometer. In some embodiments, the flow chamber includes an outlet downstream of the internal surface on which cells are immobilized. Liquid flows through the flow chamber and toward the outlet, and transports cells selectively released from the surface to the outlet. The selective release of cells can be metered such that the released cells arrive at the outlet one at a time. Alternatively, metering can be performed such that at most 2, 5, or 10 cells arrive at the outlet simultaneously.

The flow chamber can have any desired geometry or dimensions, and can be made of any convenient materials. In some embodiments, the internal surface on which the plurality of cells is initially immobilized, or the surface on the opposite side of the flow chamber, is transparent. When a trapping potential is applied in the form of an optical trap, at least one transparent surface is needed for laser light to penetrate the flow chamber. A transparent surface can also generally be useful in the present methods for observing the immobilized cells. Such observations can be used to select cells for release or to determine the locations of cells on the surface, so that light used to generate a trapping potential or induce photocatalysis can be properly directed. Any appropriate equipment, including but not limited to a microscope, camera, detector, or image processor can be coupled to the flow chamber to facilitate observations of cells on the surface.

Cells can be selected for release using any basis or criteria. For example, cells that are larger than a certain size can be released from the surface and cells that are smaller can be retained. All cells initially immobilized on the surface can be released in turn, or only a subset can be released if desired. Cells can also be released in any order. For example, cells determined to lack a characteristic of interest can be released first and disposed of downstream, and then cells possessing the characteristic can be released and further analyzed. Alternatively, cells determined to be most of interest can be released first, with less interesting cells released later or not at all, depending on the results of downstream analysis of the first cells released.

In some embodiments, the present methods further include the step of detecting a signal from one or more cells immobilized on the internal surface of the flow chamber, and selectively releasing the cells based upon the signal. The signal can arise from a fluorescent or colored label, for example, and can result from the label binding to the surface of a cell. Alternatively, the signal can result from penetration of a cell's plasma membrane by a dye and reflect the integrity of the membrane. Other kinds of signals detectable from individual cells will be apparent to those of skill in the art. In various embodiments, the signal reflects the cell cycle phase, viability, or cell type of the one or more cells, or gene expression in the one or more cells. Signals can be detected from immobilized cells using any convenient procedures and instrumentation. As desired, these signals can be coupled to means for releasing the cells, such as light sources for applying trapping potentials or inducing photocatalysis, and can be used to automate release.

IV. Systems

Systems are also provided herein for carrying out the methods described above. A system can include a flow chamber plus any means necessary or convenient for immobilizing cells on an internal surface of the flow chamber, selectively releasing cells from the surface, and flowing liquid through the flow chamber to transport the released cells. These means can include a light source and photosensitive materials (e.g. electrodes), as discussed above, for imposing a trapping potential or inducing photocatalysis, plus any associated optics, electronics, power sources, controllers, processors, hardware, or software. The system can also include liquid-handling components connected to the flow chamber, and instrumentation for observing, analyzing, or detecting signals from cells, when immobilized in the flow chamber or after selective release. If desired, the light source and instrumentation can be operatively coupled, and procedures for immobilizing and selectively releasing cells can be automated. Other features and elaborations of systems within the scope of the present application will be apparent in view of the disclosure above.

All documents (for example, patents, patent applications, books, journal articles, or other publications) cited herein are incorporated by reference in their entirety and for all purposes, to the same extent as if each individual document was specifically and individually indicated to be incorporated by reference in its entirety for all purposes. To the extent such documents incorporated by reference contradict the disclosure contained in the specification, the specification is intended to supersede and/or take precedence over any contradictory material.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the invention being indicated by the following claims.

What is claimed is:

1. A method of transporting a plurality of cells through a flow chamber, the method comprising:
   immobilizing the cells on an internal surface of the flow chamber, wherein the immobilizing comprises adhering the cells to the internal surface;
   selectively releasing the cells from the internal surface of the flow chamber, wherein the internal surface comprises an electrode, and wherein the releasing comprises applying a releasing trapping potential arising from an electric field gradient generated using the electrode; and
   flowing liquid through the flow chamber such that the released cells travel with the liquid, thereby transporting the cells through the flow chamber.

2. The method of claim 1, wherein immobilizing the cells further comprises applying an immobilizing trapping potential.

3. The method of claim 2, wherein selectively releasing the cells further comprises removing the immobilizing trapping potential.

4. The method of claim 2, wherein the immobilizing trapping potential arises from an electric field gradient.

5. The method of claim 4, wherein the immobilizing trapping potential results from dielectrophoresis.

6. The method of claim 4, wherein the electrode is photoconductive and the immobilizing trapping potential is supplied by optoelectronic tweezers.

7. The method of claim 2, wherein the immobilizing trapping potential arises from an optical field gradient.

8. The method of claim 1, wherein the internal surface of the flow chamber comprises a photocatalytic material, and wherein selectively releasing the cells further comprises illuminating the surface.

9. The method of claim 8, wherein selectively releasing the cells further comprises generating hydroxyl radicals or inducing a pH change in the vicinity of the surface.

10. The method of claim 1, wherein the cells are adherent.

11. The method of claim 1, wherein the cells are non-adherent.

12. The method of claim 1, wherein the cells are released one at a time.

13. The method of claim 1, wherein the flow chamber comprises an outlet, the liquid is flowed toward the outlet, and the released cells arrive at the outlet one at a time.

14. The method of claim 1, wherein the internal surface of the flow chamber is transparent.

15. The method of claim 1, further comprising detecting a signal from one or more cells immobilized on the internal surface of the flow chamber, wherein the cells are selectively released from the internal surface of the flow chamber based upon the signal.

16. The method of claim 15, wherein the signal reflects the cell cycle phase of the one or more cells.

17. The method of claim 15, wherein the signal reflects the viability of the one or more cells.

18. The method of claim 15, wherein the signal reflects the cell type of the one or more cells.

19. The method of claim 15, wherein the signal reflects gene expression in the one or more cells.

* * * * *